United States Patent [19]

Parker et al.

[11] Patent Number: 5,533,139
[45] Date of Patent: Jul. 2, 1996

[54] COATING DENSITY ANALYZER AND METHOD USING IMAGE PROCESSING

[75] Inventors: H. Galen Parker, Rochester; Douglas S. Finnicum, Webster; Richard D. Young, Fairport, all of N.Y.

[73] Assignee: Eastman Kodak Company, Rochester, N.Y.

[21] Appl. No.: 304,603

[22] Filed: Sep. 12, 1994

Related U.S. Application Data

[63] Continuation of Ser. No. 891,318, May 29, 1992, abandoned.

[51] Int. Cl.$^6$ .................................................. G01N 21/00
[52] U.S. Cl. .......................... 382/108; 382/141; 356/382; 356/430; 250/559.07; 250/559.28
[58] Field of Search ...................................... 382/108, 141; 356/381, 382, 429, 430; 250/559.01, 559.03–559.08, 559.27, 559.28

[56] References Cited

U.S. PATENT DOCUMENTS

| | | | |
|---|---|---|---|
| 3,582,219 | 6/1971 | Pfeifer et al. | 356/202 |
| 3,614,241 | 10/1971 | Sanford et al. | 356/175 |
| 3,814,943 | 6/1974 | Baker et al. | 250/550 |
| 3,868,510 | 2/1975 | Murata et al. | 250/572 |
| 3,873,201 | 3/1975 | Amano | 355/77 |
| 3,887,281 | 6/1975 | Kurita et al. | 250/571 |
| 3,932,023 | 1/1976 | Humer | 350/96 C |
| 3,976,382 | 8/1976 | Westby | 256/120 |
| 4,005,281 | 1/1977 | Faulhaber et al. | 235/151.3 |
| 4,120,582 | 10/1978 | DeVries et al. | 356/73 |
| 4,183,666 | 1/1980 | Tahara et al. | 356/73.1 |
| 4,224,513 | 9/1980 | Casey et al. | 250/571 |
| 4,292,672 | 9/1981 | Southgate | 364/507 |
| 4,299,451 | 11/1981 | Task et al. | 350/407 |
| 4,320,967 | 3/1982 | Edgar | 356/429 |
| 4,439,038 | 3/1984 | Mactaggart | 356/408 |
| 4,565,444 | 1/1986 | Mactaggart | 356/73 |
| 4,603,956 | 8/1986 | Baker | 354/298 |
| 4,644,174 | 2/1987 | Ouellette et al. | 250/572 |
| 4,663,522 | 5/1987 | Welbourn et al. | 250/223 |
| 4,724,481 | 2/1988 | Nishioka | 250/572 |
| 4,730,213 | 3/1988 | Kelly et al. | 358/107 |
| 4,776,692 | 10/1988 | Kalawsky | 356/239 |
| 4,810,872 | 3/1989 | Murakoshi et al. | 250/225 |
| 4,868,383 | 9/1989 | Kurtz et al. | 250/228 |
| 4,883,963 | 11/1989 | Kemeny et al. | 250/339 |
| 4,922,337 | 5/1990 | Hunt et al. | 358/101 |
| 4,931,657 | 5/1990 | Houston et al. | 250/559 |
| 4,946,282 | 8/1990 | Task | 356/432 |
| 4,955,720 | 9/1990 | Blecha et al. | 250/571 |
| 4,989,973 | 2/1991 | Noso et al. | 356/239 |
| 5,040,057 | 8/1991 | Gilblom et al. | 358/101 |
| 5,045,135 | 9/1991 | Meissner et al. | 382/8 |
| 5,068,799 | 11/1991 | Jarrett, Jr. | 356/430 |
| 5,113,454 | 5/1992 | Marcantonio et al. | 382/27 |
| 5,440,648 | 8/1995 | Roberts et al. | 382/8 |

FOREIGN PATENT DOCUMENTS

| | | |
|---|---|---|
| 0048568 | of 1982 | European Pat. Off. . |
| 54-74792 | of 1979 | Japan . |
| 61-223605 | 4/1986 | Japan . |
| 63-134941 | of 1988 | Japan . |
| 1-25038 | of 1989 | Japan . |
| 1-253641 | of 1989 | Japan . |
| WO91/14173 | of 1991 | WIPO . |

OTHER PUBLICATIONS

Thorpe et al., "New Advances in CCD Imaging," SMPTE Journal, 97, No. 5, pp. 378–387, May 1988.

John W. V. Miller, "Illumination Invariant Image Processing Techniques", Proceedings of Vision '85, Mar. 1985, pp. 3–24 to 3–37.

Vargas et al., "Solving the Photographic Negative Inspection Problem", Photonics Spectra, Jun. 1991, pp. 183–184.

*Primary Examiner*—Stephen Chin
*Assistant Examiner*—Timothy J. May
*Attorney, Agent, or Firm*—Clyde E. Bailey, Sr.

[57] ABSTRACT

An image processor based system and method are provided for recognizing predefined-types of coating density imperfections in a web. Specific imperfection-types to be analyzed include continuous-type, as well as point-type, anomalies. Continuous-type imperfections are recognized in a moving continuous web through the accumulation and integration of density data on the web passing through a system imaging area. Depending upon the type of imperfection to be imaged, the light source provides either constant illumination or strobed illumination of the moving coated web. For most types of imperfections, transmissive illumination of the web is used, however, for point-type anomalies reflective illumination is possible, particularly if the web is static. A machine vision image processor contains predefined lookup tables which allow adaptive control of web illumination within the imaging area. An integrating sphere is used to provide for uniform web illumination. Corresponding machine vision based imperfection recognition processing routines are also described.

35 Claims, 13 Drawing Sheets

5,533,139

COATING DENSITY ANALYZER AND METHOD USING IMAGE PROCESSING

This application is a continuation of application Ser. No. 07/891,318, filed May 29, 1992 now abandoned.

BACKGROUND DESCRIPTION

1. Technical Field

This invention relates in general to the detection of coating imperfections on a coated web and, more particularly, to a system and method for recognizing predefined-types of coating imperfections in a web through the acquisition of optical density variation information, for example, from a moving, continuous web substantially uniformly, transmissively illuminated.

2. Background Art

Research and development efforts in the photographic materials and paper materials industries often focus on various types of imperfections in a moving coated web. These imperfections may, for example, result from disturbances in the coating process, such as may occur during the sensitization of photographic film. Research and development efforts attempt to isolate, through process modeling, the source of an on-going disturbance-type in a coating process. Coating imperfections of particular interest to the industries are continuous-type imperfections and point-type imperfections. These imperfection types, which can occur in one or more coating levels on a support web, are typically indicative of a disturbance or design related problem in the coating process.

An effective on-line imperfection recognition system and method would enable one to discern, characterize and confirm various models of the coating process, thereby determining the disturbance causing such an imperfection. Two significant issues, however, must be addressed by any imperfection recognition system before adequate optical data can be collected from sensitized coatings under examination. First, the system must be able to extract small density changes from the obtainable spatial and temporal noise background. Secondly, the system must provide adequate illumination within the spectral bandwidth of the usable contrast range, while avoiding solarization of any sensitized web.

State-of-the-art efforts to quantize moving web disturbances have most commonly been implemented as laser scanning systems. For example, continuous laser beams are often swept by multifaceted polygon mirror scanners across moving webs of film or paper support, and focused with dedicated optics onto a discrete detector such as a photomultiplier tube. Various detector configurations enable data acquisition in either a reflective or transmissive mode. Unfortunately, such laser scanner packages can be expensive and typically have limited anomaly detection capabilities.

Specifically, such laser scanning packages are almost universally unable to process data associated with very narrow lines and streaks which may be imbedded in the signal noise background. (Also, laser scan output processing packages, in general, remain less sophisticated than those accompanying state-of-the-art imaging technologies such as solid state cameras.) Therefore, a need is recognized to exist today in the photographic and paper materials industry for a more effective and less expensive technique to extract and characterize imperfections from background data including inherent noise variations, and particularly low-level, narrow continuous-type imperfections in a moving coated web.

SUMMARY OF THE INVENTION

Briefly described, the present invention comprises in one embodiment an image processor based system having several novel aspects. In a first novel aspect, the system includes an imaging area within which a predefined continuous-type density imperfection in a moving web is recognized. A light source is provided for substantially uniform illumination of the web while the web is passing through the imaging area. Full frame acquisition and integration means accumulate density data on the illuminated web and produce integrated image data representative thereof. An image processor is coupled to the image acquisition and integration means and programmed to recognize the predefined continuous-type density imperfection in the web using the produced integrated image data.

In another aspect, the image processor based system of the present invention is capable of recognizing any predefined-type of density imperfection in a web positioned within a defined imaging area. This system comprises web illumination means including an integrating sphere having an output positioned adjacent to the system imaging area. The integrating sphere provides at its output substantially uniform transmissive illumination of the web positioned within the imaging area. Image acquisition means accumulates density data from the illuminated web and outputs image data representative thereof. An image processor is coupled to the image acquisition means and programmed to recognize the predefined-type of density imperfection in the web using the image data output by the image acquisition means.

In a further version, the image processor based system recognizes any predefined-type of density imperfection in a web positioned within the imaging area. The system includes a light source having an output aperture through which is provided a substantially uniform transmissive illumination of the web within the imaging area. Coupled to the light source is a light level control means for varying the illumination intensity passing through the output aperture, to thereby control the intensity of the uniform transmissive illumination of the web within the imaging area. Image acquisition means accumulates density data on the illuminated web and outputs image data representative thereof. An image processor is coupled so as to control the light level control means and receive the output of the image acquisition means. The processor is programmed to recognize the predefined-type of density imperfection in the web using the image data output from the image acquisition means. Various specific additional structure associated with each aspect of the system embodiments summarized above are also disclosed and claimed herein.

In yet another aspect, the present invention comprises a recognition method for identifying density imperfections of a predefined-type in a moving web passing through the imaging area. The recognition method includes the steps of: substantially uniformly illuminating the web while it is passing through the imaging area; acquiring density data from the illuminated web passing through the imaging area; integrating the accumulated density data and producing therefrom integrated image data; and recognizing the density imperfection of predefined-type from the integrated image data produced. As with the system embodiment, various specific process enhancements are also described and claimed herein.

To summarize, an image processor based technique is set forth, capable of imaging and analyzing any predefined-type of density imperfection in a moving coated web, including two-dimensional and one-dimensional imperfections. Specific density imperfections to be imaged include continuous-type and/or point-type imperfections. The technique described, whether system or process, can resolve variations in optical density of 0.0005 optical density units. Significantly improved signal-to-noise characteristics over any prior art implementation are obtained. Real time logarithmic image acquisition is utilized while still maintaining high processing performance and system/process flexibility. On-line compensation for illumination and sensor nonuniformity is featured, and the technique is readily implementable by one skilled in the art, requiring only moderate cost expenditure.

BRIEF DESCRIPTION OF THE DRAWINGS

These and other objects, advantages and features of the present invention will be more readily understood from the following detailed description of certain preferred embodiments thereof, when considered in conjunction with the accompanying drawings in which.

DESCRIPTION OF THE PREFERRED EMBODIMENTS

As noted initially herein, the present invention is directed to an automated imaging system and method, principally for use by research and development facilities, to recognize imperfections in a sample of web material, such as a test photographic film or a test paper web. The invention is described in detail herein in connection with the analysis of a predetermined imperfection-type, such as continuous-type imperfections in a moving, sensitized film support. However, those skilled in the art will recognize that the invention is not limited to the specific type of web described, or to whether the web is moving or fixed. Further, various uses/enhancements are readily conceivable by one skilled in the art, all of which are intended to be encompassed by the appended claims.

An imaging system based on detection of reflective light off a moving web material is effective for certain surface coating imperfections. However, in products having multiple coating layers, with the possibility of covered layer imperfections, detection of anomalies using transmissive lighting provides for more efficient image analysis. Therefore, the following discussion centers on a coating density analyzer, and an accompanying method, dedicated to a transmissive web lighting approach.

Figure 1:
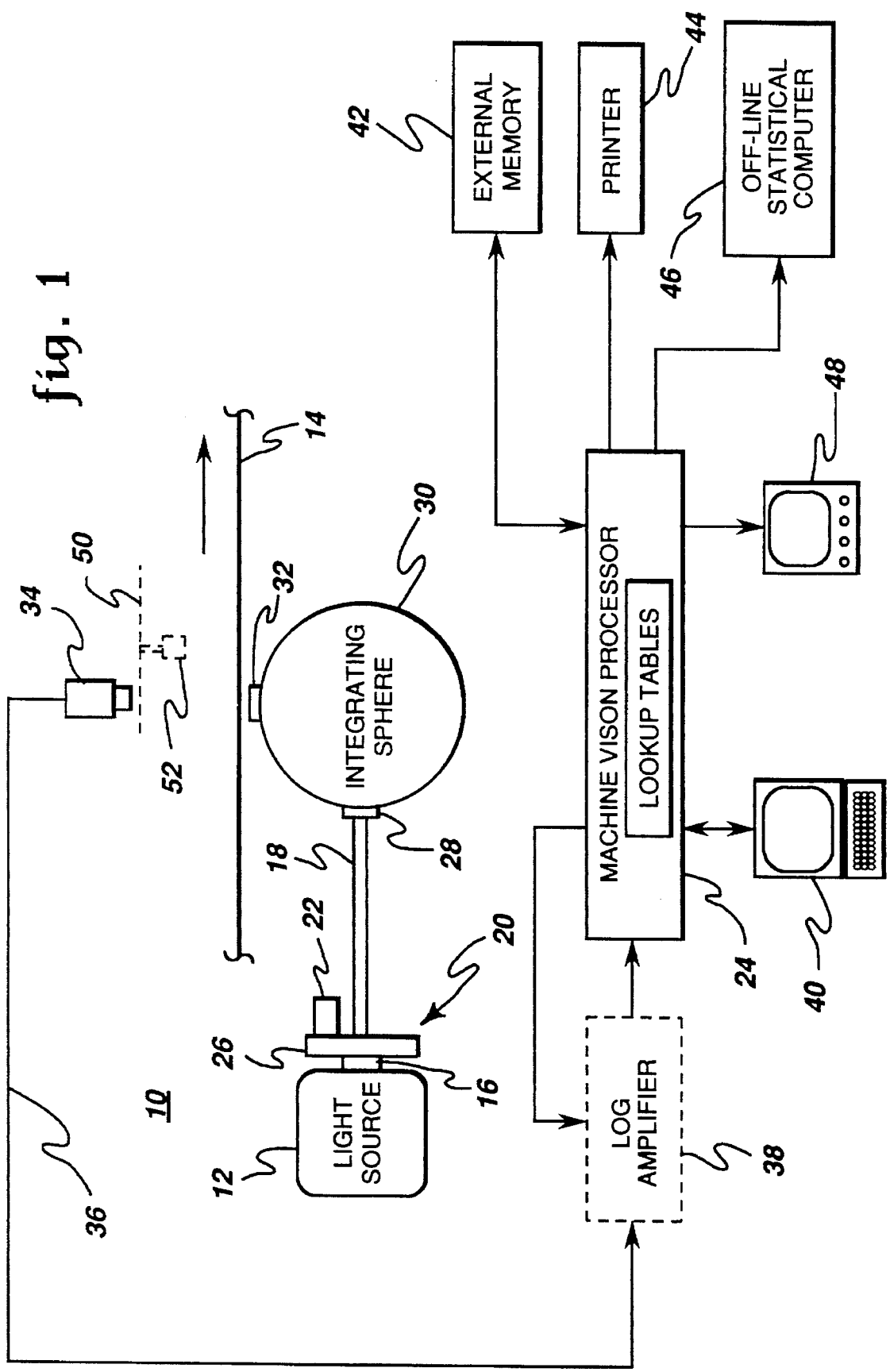
FIG. 1 is a partial diagram of one embodiment of a coating density analyzer pursuant to the present invention.

FIG. 1 depicts one embodiment of a coating density analyzer, generally denoted 10, constructed pursuant to the present invention. Analyzer 10 includes a light source 12 which supplies transmissive illumination to a moving, coated support web 14 to be analyzed. Light source 12 may comprise either a temporally constant uniform source, or a strobe source, for the capture of discrete web images. Selection of such a constant or a strobed light source depends upon the particular predefined-type of density imperfection to be recognized/analyzed. For example, a strobe light source is preferred for recognition of spot-type imperfections in a moving web, while a constant light source is preferred for detection of continuous-type imperfections. The strobe light source may comprise any commercially available such device, while a constant light source preferably comprises a tungsten halogen light source.

Light is transmitted from source 12 through an output port 16 to a fiber-optic link 18 via an adjustable illumination intensity filter assembly 20. Filter assembly 20 includes a stepping motor 22, which is connected to a system coordinating processor (such as a machine vision based processor 24). The system coordinating processor controls via the stepping motor a light aperture 26 of filter assembly 20 positioned over port 16. In one specific embodiment, intensity control is obtained by modulating the light entering the fiber-optic link with a stepping motor driven aperture (not shown). The modulation aperture 26 is designed to transmit a somewhat linear change in illumination intensity in response to equally spaced steps of computer input values to the drive device. If desired, the aperture design may be tailored to also accommodate non-linear transfer functions.

Link 18 is optically coupled to an input 28 of an integrating sphere 30. Sphere 30 may comprise any commercially available integrating sphere appropriately configured for the function described herein. For example, Labsphere, Inc. of North Sutton, N.H., has a number of commercially available sphere assemblies with appropriate internal surface coatings which will produce substantially uniform diffuse illumination at an output 32. Output 32 is disposed parallel to moving web 14. Coated web 14 is transported within close proximity (for example, 1–2 cm) to integrating sphere 30 exit aperture 32.

A two-dimensional 512×512 pixel CCD camera 34 is used to acquire images of the moving web material illuminated in transmission within a defined imaging area. (However, depending upon the type of imperfection to be imaged, a one-dimensional camera may be sufficient.) Preferably, camera 34 includes horizontal and vertical synchronization, along with an integration function. One preferred commercially available camera is marketed by Pulnix America, Inc. of Sunnyvale, Calif., as a Pulnix TM-845 CCD Camera. This particular camera includes an integrating capability, provides a good signal-to-noise ratio and utilizes a cooled element to minimize thermally induced noise.

The presence of an integration function in the selected imaging camera is important to one aspect of the invention, i.e., to the imaging (and automated recognition) of continuous-type imperfections in the moving coated web material 14. An integration function naturally averages random temporal and spatial variations for enhanced signal-to-noise performance. In addition, with integration comes the capability for system operation at extremely low illumination levels, thereby preserving any sensitometric characteristics of the coated web, e.g., if the web comprises coated photographic material. Analog images from CCD camera 34 are fed by a line 36 connecting the camera to the processor 24, which typically includes front-end processing to amplify and offset the received signal. Optionally, integrated output from CCD camera 34 could be routed through a 12-bit digital video linear/log amplifier 38 (shown in phantom), offset and amplified for expanded gray scale analysis, and then directed to the machine vision based processor platform. Optional log amplifier 38 is described further below in connection with FIG. 6.

Any one of a number of commercially available image processing units could be used to implement processor 24. One preferred processor is marketed by Applied Intelligent Systems of Ann Arbor, Mich. as an AIS-4000 Vision Processor. The AIS-4000 vision platform provides exceptional image processing speed, competitive pricing and an extensive binary and gray level morphological processing package. The AIS-4000 is equipped with multiple serial communication ports, digital I/O, nonvolatile user memory, and an SCSI hard disc interface connection. The serial processor ports are initially connected to a host computer (e.g., a PC workstation 40), light modulating aperture drive motor 22, and a filter wheel drive associated with the camera (described below). Input/output connections can include couplings to an external memory 42 (for storing image data), a printer 44 (for printing image data), an off-line statistical computer 46 (for conducting statistical computations on image data), and/or a video monitor 48 (for operator viewing of images).

As noted, the external video amplifier 38 may be used for performing 12-bit transfer functions. However, when only 8-bit resolution is required, the image processor video amplifier and lookup tables may be used instead. The image processor video amplifier also features software programmable gain and offset. Further, illumination shading compensation can be achieved by subtraction of a suitable reference image from subsequent inspection images. The compensated image is operated on by classical and morphological image processing algorithms to further reduce any remaining noise components, normalize the background and extract low-level density imperfection information (discussed further below). The signal-to-noise ratio is preferably also enhanced by the use of fastidious grounding methodology, ample shielding where appropriate, powerline isolation and inline filtering.

Figure 2:
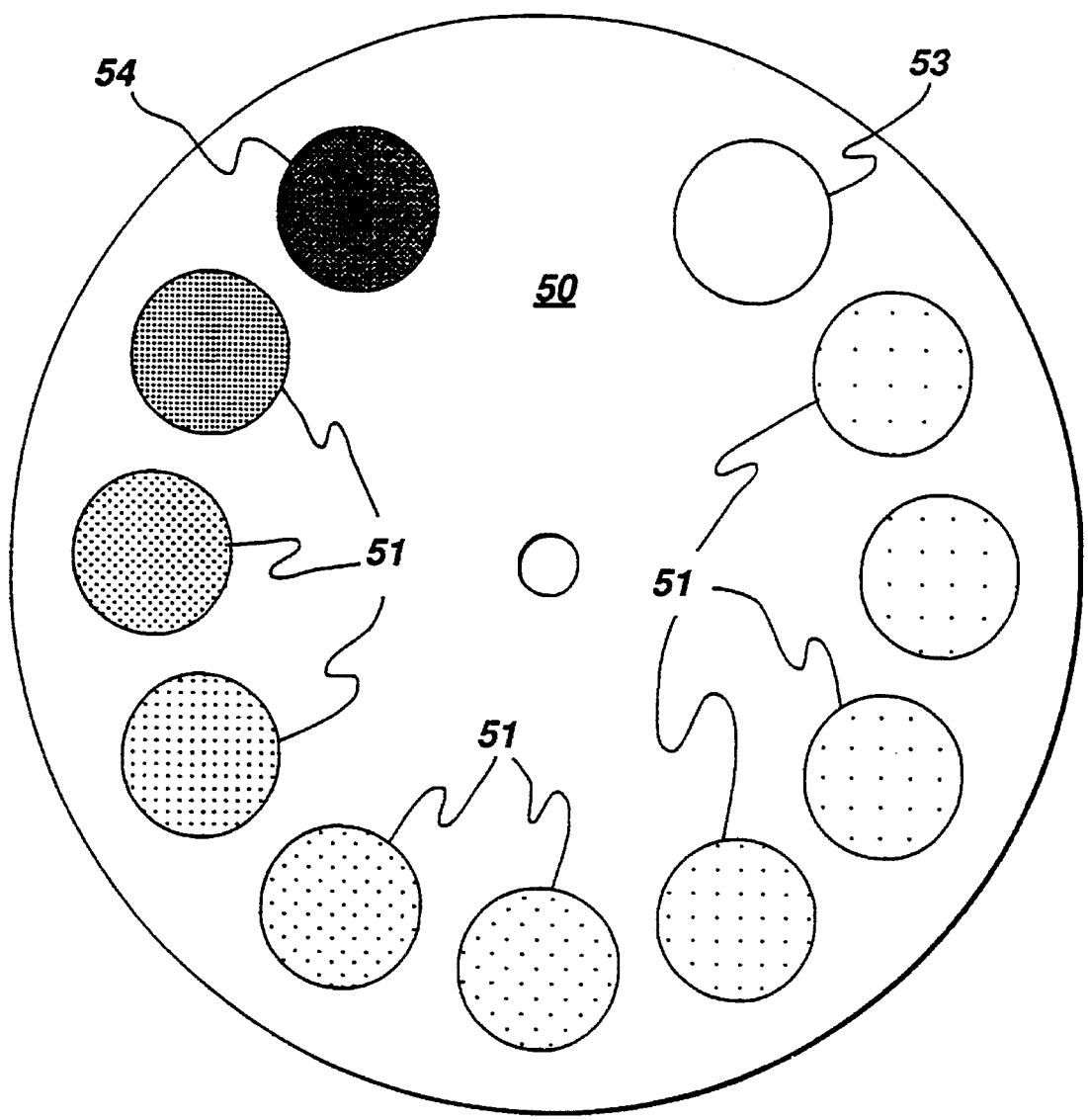
FIG. 2 is one embodiment of a neutral density filter wheel used pursuant to the present invention to characterize an intensity transfer function for the coating density analyzer of FIG. 1.

A variable illumination aperture size and intensity lookup tables are employed to enable adaptive on-line illumination control for a range of target web densities. Measurements from an illumination sampling circuit permit the computation of normalized scene-to-scene intensity values. Pursuant to the depicted embodiment of the present invention, an illumination lookup table is constructed utilizing a rotating neutral density filter wheel 50 which is initially disposed between the moving support web 14 and the imaging camera 34. FIG. 2 depicts one embodiment of such a rotatable neutral density filter wheel 50.

A number of windows 51 are provided in the wheel, within each of which is a neutral density filter ranging in value from 0 to 2.0 optical density units in 0.2 optical density increments. A first window 53 contains no filter, and thereby yields a neutral density value of 0, while a last window 54 contains the greatest extent of light filtering, i.e., a filter of 2.0 optical density units. The upper limit of the optical density range, i.e., 0 to 2.0, will vary with the density of photographic film or paper material to be imaged. Rotatable filter wheel 50 is driven by a computer controlled motor 52 (FIG. 1).

Figure 3:
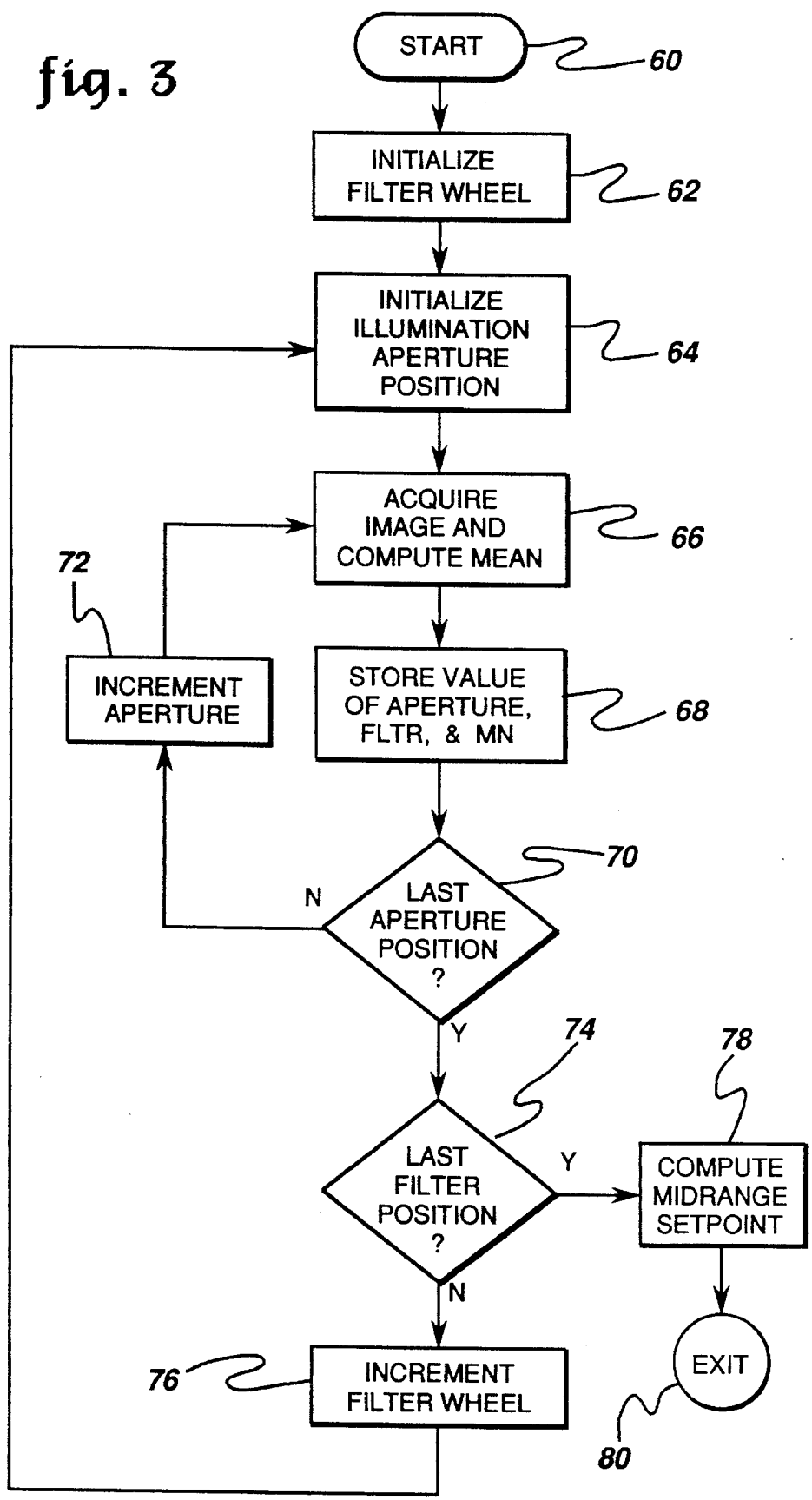
FIG. 3 is a flowchart of one processing embodiment for creating an illumination level lookup table pursuant to the present invention.

To adequately cover a possible density range of 0 to 2.0 units, a software lookup table is pregenerated and stored in processor 24 to assist in on-line adaptive control of the aperture illumination filter assembly 20. The lookup table values of gray level histogram means are initially generated by correlated stepping of the illumination control aperture (26) and the neutral density filter wheel (50). An overview of one embodiment of this process is depicted in FIG. 3.

As shown, processing for creation of an illumination lookup table begins, 60 "Start," with initialization of the optical density filter wheel, 62 "Initialize Filter Wheel." Again, a 0 to 2.0 optical density range is used by way of example only for the moving web material to be transmissively illuminated and imaged. (Unless otherwise noted, all optical components are assumed fixed during the creation of the optical lookup table.) Next, the illumination aperture position is initialized, 64 "Initialize Illumination Aperture Position." For example, processing may begin with full illumination being output from the light source, i.e., with the optical cross-section of the fiber-optic interconnect at full illumination. (Also, an even number of stepping motor increments are preselected between aperture positions.)

The CCD camera then obtains an image and a corresponding histogram mean is computed, 66 "Acquire Image and Compute Mean." The computed histogram mean, along with the corresponding illumination aperture position and filter wheel position are stored, 68 "Store Value of Aperture, Fltr, & Mn," and inquiry is made whether the instantaneous illumination aperture position is the last aperture position in the initialized range, 70 "Last Aperture Position?" If "no", then the illumination aperture position is incremented, 72 "Increment Aperture," a new image is acquired and a corresponding histogram mean is computed.

Once the last illumination aperture position is reached for the instantaneous filter wheel position, inquiry is made whether the filter wheel is at its last initialized position, 74 "Last Filter Position?" If "no", then the filter wheel is incremented, 76 "Increment Filter Wheel" and the illumination aperture position is reinitialized at instruction 64. Once the last filter position is reached, then a midrange setpoint is calculated for each filter curve, 78 "Compute Midrange Setpoint." The midrange setpoint is described further below. Subsequent setpoint computation, and predefinition of the illumination lookup table is completed and processing terminates, 80 "Exit."

Figure 4:
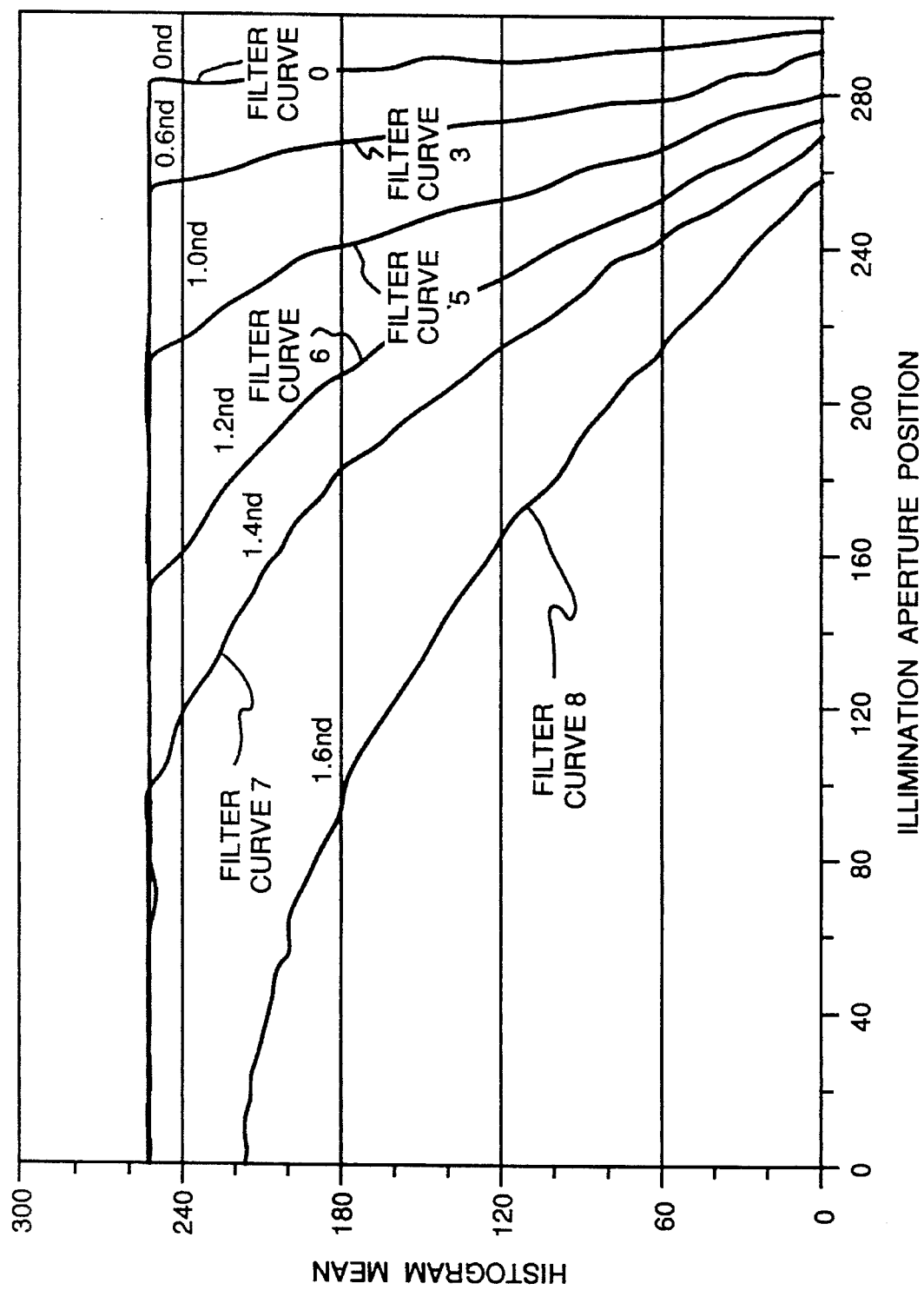
FIG. 4 is a graphical representation of sample lookup table values (curves) wherein image gray scale histogram means (for selected neutral density filters) are plotted versus illumination aperture position.

FIG. 4 graphically depicts typical illumination lookup table characteristics. In FIG. 4, the histogram mean (i.e., average number of gray levels e.g., in a specified pixel array) is plotted against the "illumination aperture position" which is scaled from a full-open to a substantially closed position at increment 300. Six neutral density filter curves are plotted by way of example, namely, 0 nd (filter curve 0), 0.6 nd (filter curve 3), 1.0 nd (filter curve 5), 1.2 nd (filter curve 6), 1.4 nd (filter curve 7), & 1.6 nd (filter curve 8). These are the transfer functions for corresponding a family of neutral density filters.

Acquisition of images within an illumination distribution faithful to an original scene is significantly effected by three system factors, namely, spatial intensity variations in the light source, optical effects, and fixed pattern sensor noise. These nonuniformities, when superimposed on an acquired image, may complicate the task of discerning low level density imperfections.

Figure 5A:
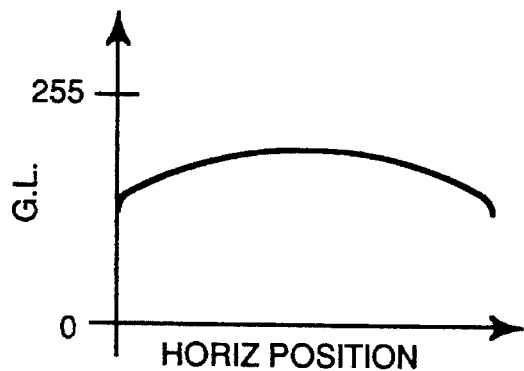
FIGS. 5(a)–5(d) are graphical representations of a multiplicative image compensating algorithm pursuant to the present invention.
Figure 5B:
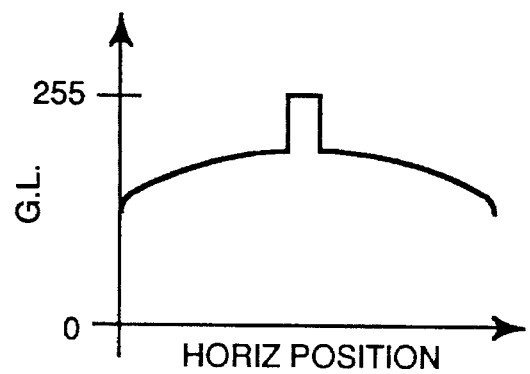
Figure 5C:
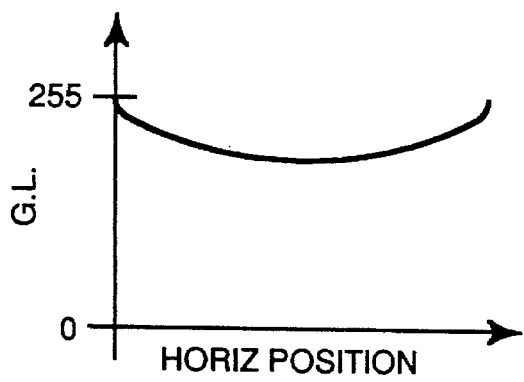
Figure 5D:
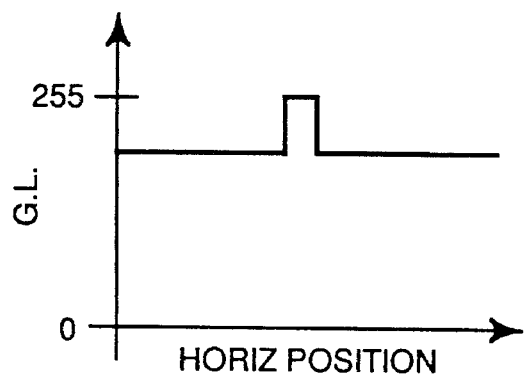

One means for compensating for illumination nonuniformities is to generate and retain an optical reference, i.e., an image of the field-of-view of interest, without the presence of sample target imperfections. Subsequent sample images acquired from within the same field-of-view are then multiplied by an inverted normalized image in the optical reference to yield a fully compensated scene. Multiplicative compensation is demonstrated in FIGS. 5(a)–5(d), which generically depict illumination compensation. As shown therein, a reference scene signature is first recorded, free of any coated film. Gray level values for a single row of reference signature data are graphed in FIG. 5(a). This graph portrays brightness levels for imperfect illumination as would be viewed at the camera output. FIG. 5(c) plots an inversion of the normalized reference profile. FIG. 5(b) depicts by way of example, a coated film sample with a continuous-type imperfection profile, illuminated by the same nonuniform light source. After multiplying the sample data by the inverted normalization of the optical reference, and applying a scaling factor, a fully compensated image is obtained as displayed in FIG. (d).

The multiplicative approach can effectively be implemented in software, but may consume an unacceptable amount of time using certain available image processing equipment. Hardware frame multiplication is generally faster; however, the necessary scaling to prevent 8-bit gray value overflow consumes valuable dynamic range. If one converts the expressions to logarithmic form, compensation may be accomplished with frame subtraction. This is illustrated below.

Let: Tr=Transmittance of the reference
Let: Ts=Transmittance of the sample image
Then: Ts * 1/Tr (Compensation Formula)
However: Log[Ts]+log[1/Tr]=log[Ts]–log[Tr]
So: Ts * 1/Tr=Antilog {log[Ts]–log[Tr]} (Compensation Formula)

The compensation algorithm is thus expressed as a subtraction of the log video reference frame from the log video sample frame. Therefore, timely illumination compensation is accomplished with a single frame subtraction operation, Furthermore, the image data is in the desired density form for the coating analyzer application.

Again, a logarithmic signal is specified for two reasons. First, studies indicate that variations in coating density, and optical density itself are a log function. Secondly, the log of the image data can be used to implement an effective real-time compensation technique for fixed pattern illumination nonuniformities. The compensation technique is discussed further herein. Given the limitations of existing options, a dedicated 12-bit prime-based lookup table for deriving log values from video data has been devised. In order to quantize a standard video signal, a modest amount of preprocessing is required.

Figure 6:
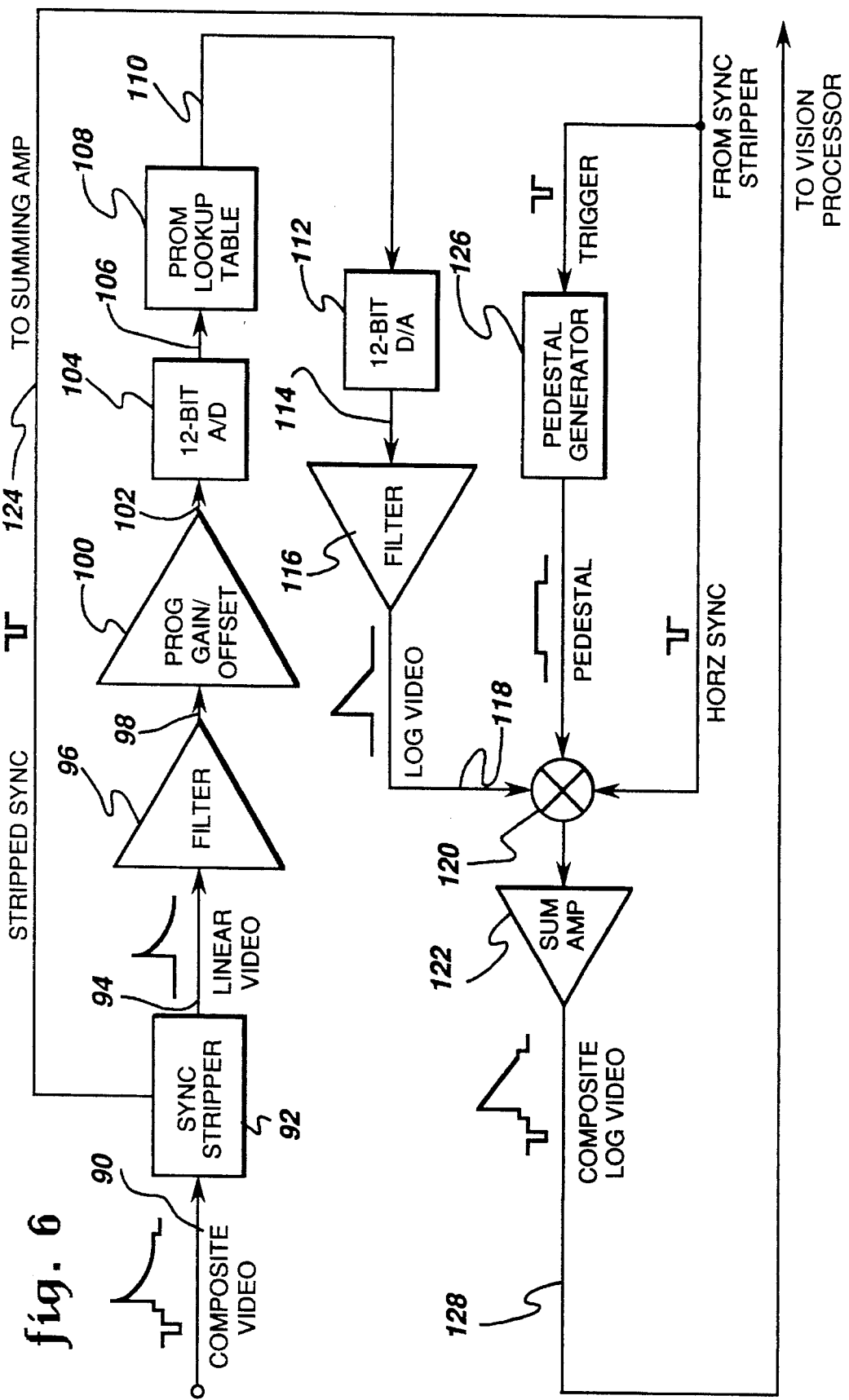
FIG. 6 is a block diagram of one embodiment of a 12-bit digital video logarithmic amplifier for use in an alternate embodiment of the coating density analyzer of FIG. 1.

FIG. 6 illustrates one embodiment of a log amplification circuit 38 (FIG. 1) wherein a composite video image comprising an RS-170 video format for a single horizontal scan is input on line 90 to a sync stripper 92. Sync stripper 92 clamps the dark level pedestal to ground, and separates sync pulses and pedestal. The resultant linear video signal is output on line 94 to a low pass filter 96 and hence on line 98 to a programmable gain/offset stage which is controlled by the image processor to condition the isolated video waveform for analog-to-digital conversion. The resultant signal is fed via a line 102 to a 12-bit A/D converter 104 for 12-bit quantization.

The digitized video signal is then passed via line 106 to a PROM lookup table 108, which is configured with a number of programmable options. The simplest of these is a linear transfer function wherein the output signal transfer characteristic is identical to that of the input. Also embedded within the lookup table 108 are a logarithmic and an expanded logarithmic transfer function. In order to employ the expanded log function, the analog gain and offset 100 must be adjusted accordingly to present the correct level of expanded video signal to the analog-to-digital converter. The desired transfer function and gain/offset parameters are simultaneously selected by the image processor (see FIG. 1).

Over-specification of the dynamic bit range relative to the eight-bit vision processor minimizes truncation related precision error in the execution of the logarithmic algorithm. An Hitachi 63701B0 communication processor can be embedded within the logarithmic amplifier and configured as slave to the vision processor host. This serial communication link will permit software selection of the desired lookup table. (The sample amplified log window would be such that the gain is initially specified so as to resolve gray level elements on the order of 0.0005 optical density units about a mean density of 1.0.)

The modified digital signal is passed on line 110 to a twelve-bit D/A converter 112 for conversion back to analog form. The resultant analog signal is passed on line 114 to a low pass filter 116 and is output via connection 118 and junction 120 to a summing amplifier 122. Also input to junction 120 are the horizontal sync signal received from sync stripper 92 via line 124 and the pedestal signal from a pedestal generator 126 triggered by the signal from sync stripper 92 for the composite waveform. The resultant amplified and offset composite log video signal is output on line 128 to the image processor (FIG. 1).

Figure 7:
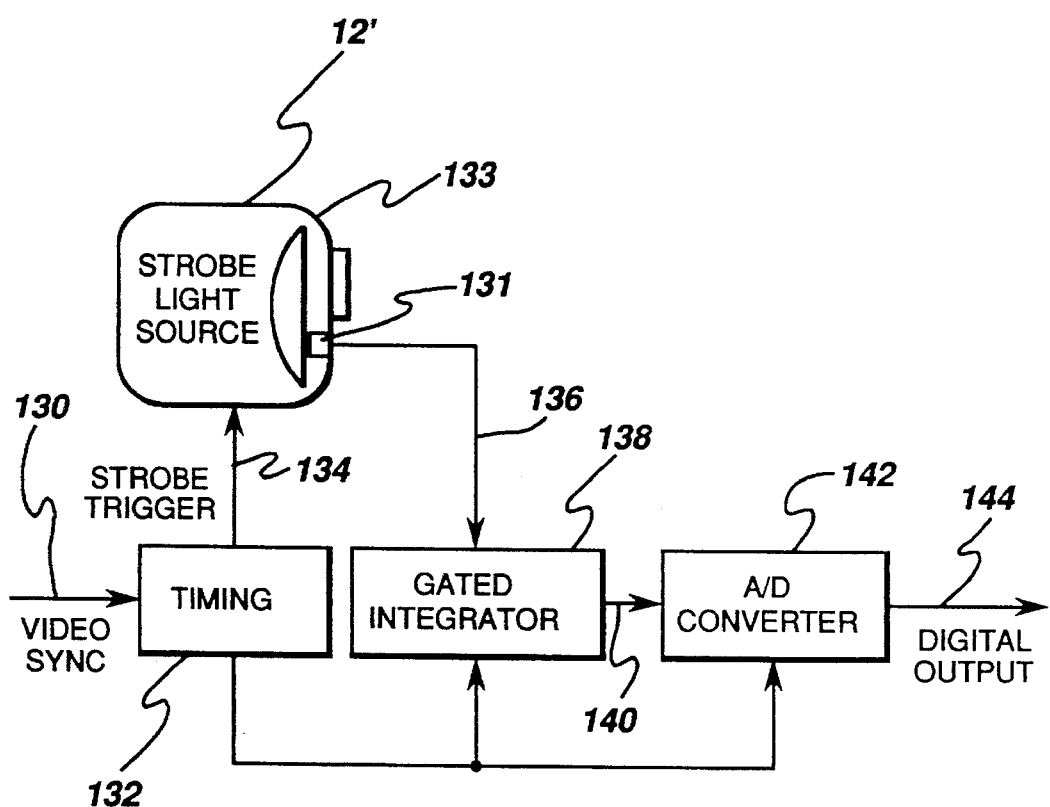
FIG. 7 is a block diagram representation of one embodiment of a strobe normalization circuit for an optional implementation of the coating density analyzer of FIG. 1 wherein a strobed light source is used.

The adaptive illumination approach described herein depends upon accurate measurement of the change in illumination levels induced solely by specific aperture movement. To support compensation for strobe instability, strobe level acquisition hardware has been designed, an overview of which is depicted in FIG. 7.

In this embodiment, strobe light source 12' includes a photosensor 131 mounted within a strobe light source housing 133. Strobe 12' is triggered by a signal on a control line 134. A current-to-voltage amplifier integral to the photosensor provides drive via line 136 to a gated integrator 138. Integrator 138 comprises a ten-bit integrator which has a quantized output that is passed to the vision processor via A/D converter 142, connect line 144 and processor digital I/O (not shown). Integrator and conversion timing 132 are derived from vertical sync pulses. It is intended that strobe values be recorded during optical reference acquisition. Subsequent flash deviations from the reference can be used to calculate related compensation factors. Strobe related drift may then be normalized within a frame by multiplying gray values by the appropriate compensation factor.

With respect to coating density analysis, the signal-to-noise (S/N) ratios of coated web perturbations as viewed in transmission, may be extremely low. Background noise may be several orders of magnitude greater than any density feature perturbation. Imperfection changes on the order of $10^{-3}$ density units or less in unexposed sensitized film may be significantly detrimental in certain processed materials. In order to effectively view such low signal levels, camera output must be amplified by as much as an order of magnitude, or an order of image quantization greater than 8-bits must be employed. The embodiment of the present invention described herein consists of the amplification approach. With concurrent noise management techniques and sophisticated signal processing, the amplified information can then be successfully extracted from a scene.

Imaging noise may present itself in a variety of forms. The more severe manifestations may be assigned to four general categories, each of which is enumerated below. With the exception of the morphological software algorithms, many of the techniques are individually known in the art. The algorithms are believed especially unique with respect to how they are implemented within a web scanning application.

Illumination-related Nonuniformities

Fixed pattern illumination nonuniformities may be found in at least three related components of the coating density analyzer. Some nonuniformity is present in the intensity distribution of the illumination source itself. Secondly, illumination-related optics may introduce spatial variations in intensity. And finally, pixel-to-pixel gain and offset variations, thermally induced effects, and clock noise all contribute to sensor-related fixed pattern nonuniformities. To suppress much of this noise, an attempt to minimize variation up front in component hardware is preferred.

For a temporally constant illumination source, a tungsten-halogen light source is coupled through a fiber-optic bundle into an integrating sphere. For the acquisition of point-type imperfections, a strobed xenon arc lamp may be coupled into the same fiber-optic bundle as for the tungsten source. Color filters and diffusing elements may be optionally introduced between the light source and the integrating sphere. A diffusing element mounted at the output end of a fiber-optic bundle contributes also to illumination uniformity. The web is transported parallel to, and near the exit aperture of the integrating sphere. The overall configuration insures that light intensity variation at the exit aperture of the sphere remains typically within one to two percent of the mean. High quality camera lenses may be employed, as well as the above noted Pulnix TM-845, 512×512 CCD camera. Again, this particular camera model exhibited a combination of several non-standard features, including: incorporation of asynchronous integration, inclusion of a peltier cooling element to reduce fixed pattern dark current by a factor of 10, and a relatively quiet video output.

In addition to strategic components selection, standard signal processing techniques are also used to minimize illumination nonuniformities. One such approach involves a background compensation scheme. If the image is acquired with no film sample present, then a signature of the fixed illumination-related nonuniformities is documented. This captured footprint is referred to as the "optical reference". Again, multiplicative techniques in transmittance space, or subtractive techniques in log space, can be used to remove the fixed pattern illumination nonuniformities common to both images (described above with reference to FIGS. 5(a)–5(d).

Web Aberrations and Nonuniformities

In a number of applications, the image of a coated web can include variations that interfere with the extraction of imperfection features. Low frequency fixed pattern noise in the web may be normalized with gray level morphological processing software. Some web coatings may exhibit high spatial frequency structure of a random nature. This type of structure may be minimized by classical filtering and non-linear morphological algorithms. If only continuous-type imperfections are to be recognized, then a combination of integration, frame averaging, and row averaging may be employed to reduce random noise, while still retaining significant information about a continuous-type imperfection.

Random Electromagnetic Noise

Random electromagnetic interference (EMI) emanates from system components as well as external sources. As with fixed pattern illumination nonuniformities, random noise is minimized prior to its appearance in the imaging system. As previously discussed, good engineering practice with respect to grounding, shielding, ac isolation, system electronics design, and power line filtering are very important for ensuring low electronic noise levels throughout the image acquisition hardware. Finally, what remains of random noise in the acquired image may be cleaned up further by use of classical and morphological image processing algorithms.

Well known video processing techniques may also be performed on the camera output. Dage-MTI of Michigan City, Ind., manufactures a camera controller that exhibits excellent S/N characteristics. If only continuous-type imperfections are to be recognized, averaging techniques again will significantly enhance image quality with respect to random noise sources.

Thermally Generated Noise

At room temperature, thermally induced sensor variables include fixed pattern dark noise (as previously discussed), and random thermal noise. Both may be effectively minimized by depressing the sensor temperature. Peltier cooling is the preferred technique for the present invention. Again, optical reference manipulation can be employed to remove the fixed pattern effects; and frame and row averaging techniques may be successfully applied, when examining continuous-type imperfections, to suppress random thermal noise effects.

Figure 8:
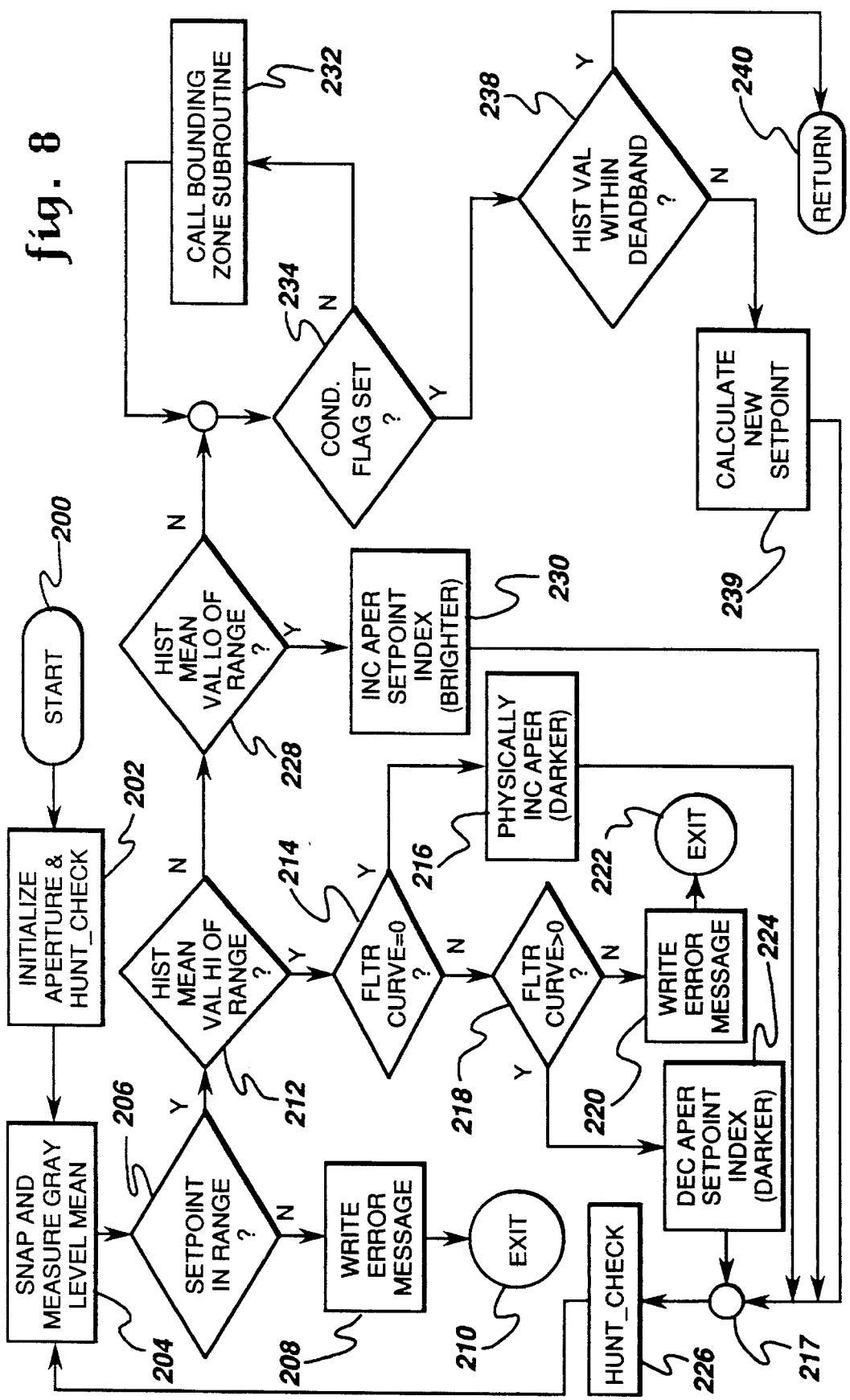
FIG. 8 is a flowchart of one embodiment of an adaptive light level process control pursuant to the present invention using the illumination level lookup tables created by the processing of FIG. 3.

One embodiment of an adaptive light level flowchart pursuant to the present invention is set forth in FIG. 8. As noted above, typical illumination lookup table characteristics include aperture mean setpoints for each neutral density range. These are the aperture positions for which the gray level histogram means of acquired image data are nominally midrange.

At the start, 200 "Start," of the adaptive illumination control sequence, the illumination aperture is initialized to a predefined position corresponding to the mean setpoint for an assumed coated web sample density value, e.g. a density value of 1.0, 202 "Initialize Aperture & Hunt_Check." (This is an empirically determined midpoint value for the range of densities typically viewed.) In addition, a counter is initialized for the hunt_check operation which will track the number of iterations through the flowchart of FIG. 8. If the number exceeds a predefined limit, then processing is discontinued. After initialization, the histogram gray value mean is extracted from the acquired coated web sample image, 204 "Snap and Measure Gray Level Mean."

In general, the adaptation algorithm determines where within the neutral density bounding curves the histogram mean lies for the tested setpoint. Initially, inquiry is made whether the setpoint is in the predefined range of setpoint values, 206 "Setpoint in Range?" If "no", an error message is written, 208 "Write Error Message," and processing is terminated, 210 "Exit." If the setpoint is not within the predefined range of lookup table values, then a significant error has necessarily occurred and processing is terminated.

Assuming that the setpoint is within the range selected, inquiry is next made as to whether the histogram mean value is high of the operating range of the lookup table, 212 "Hist Mn Val Hi of Range?" If "yes", the processor determines whether the histogram mean value coincides with the filter curve 0, 214 "Fltr Curve=0?" If the value does fall on filter curve 0, then the illumination aperture must be physically incremented to obtain darker imaging of the web, 216 "Physically Inc Aper (Darker)." After physically incrementing the aperture, processing passes to junction 217.

Assuming that the histogram mean value is not coincident with the zero filter curve, then the processor inquires whether the value is greater than the corresponding value filter curve 0, 218 "Filter Curve>0?" If "no", an error message is written, 220 "Write Error Message," and processing is terminated, 222 "Exit." Conversely, if the histogram mean value coincides with the filter curve greater than the zero curve, then the processor decrements the aperture setpoint index in the prestored lookup table to obtain a darker filter curve, 224 "Dec Aper Setpoint Index (Darker)," and passes to junction 217. From junction 217 is implemented a hunt_check routine, 226 "Hunt_Check," wherein a hunt counter is incremented and inquiry is made whether the upper predefined limit of the counter has been reached. If so, processing is terminated since the processor failed to identify a proper aperture adjustment within the predefined number of cycles.

Returning to inquiry 212, if the histogram mean value is not high of range, then inquiry is made whether the value is low of range, 228 "Hist Mn Val Lo of Range?" If "Yes", then the setpoint index is incremented to a brighter range within the lookup table, 230 "Inc Aper Setpoint Index (Brighter)," and flow is to junction 217.

Figure 9:
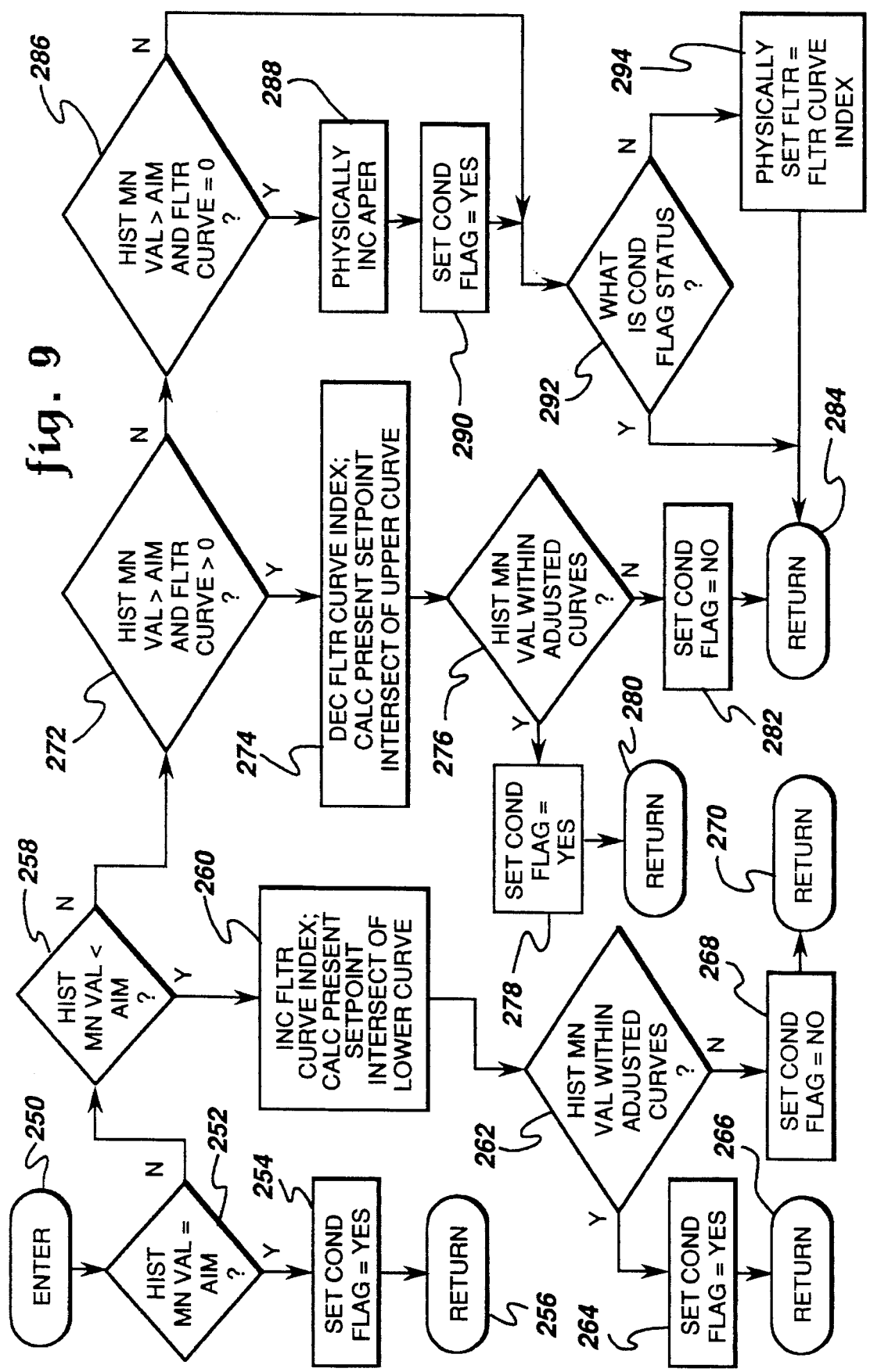
FIG. 9 is a flowchart of one embodiment of a bounding zone subroutine for the adaptive light level process control of FIG. 8.

Returning to inquiry 228, if the histogram mean value is not low of the range, meaning that the value falls within the predefined setpoint index, then inquiry is made whether condition flag is set, 234 "Cond. Flag Set?" If "no", then a bounding zone subroutine is called, 232 "Call Bounding Zone Subroutine." The subroutine, one embodiment of which is depicted in FIG. 9, attempts to define within which neutral density curves the measured histogram mean value falls. The condition flag is used as feedback to the adaptive processing routine of FIG. 8 to indicate the results of the subroutine processing. If the condition flag is set in a subroutine, then the bounding curves have been identified.

Once the condition flag has been set, then inquiry is made whether the histogram mean value is within the deadband, 238 "Hist Val Within Deadband?" If "Yes", return is made to the adaptive light level routine call point in a master routine (not shown), 240 "Return." If the histogram mean value is not within the deadband, then a new setpoint value is calculated by calling the setpoint subroutine (FIG. 10), 239 "Calculate New Setpoint," after which processing passes to junction 217. From junction 217, the processor returns to measure a new gray level mean at instruction 204, i.e., assuming that the upper limit of the Hunt_Encounter still has not been reached.

The bounding zone subroutine of FIG. 9 is next described. After entering, 250 "Enter," the subroutine, the processor inquires whether the present histogram mean value is equivalent to the predefined aim mean value, 252 "Hist Mn Val=Aim?" If "yes", the condition flag is set for the adaptive light level processing of FIG. 8, 254 "Set Cond Flag=Yes," and return is made to the main processing of the adaptive light level program, 256 "Return." Assuming that the histogram mean value does not equal the desired aim, then the processor determines whether the value is less than the desired aim, 258 "Hist Mean Val<Aim?" If "yes", then the processor increments the filter curve index within the lookup table, and calculates a present setpoint intersection for the lower filter curve, 260 "Inc Fltr Curve Index; Calc Present Setpoint Intersect of Lower Curve." Thereafter, the processor inquires whether the histogram mean value is within the present adjusted curves, 262 "Hist Mean Mn Val Within Adjusted Curves?" A condition flag is set "yes", 264 "Set Cond Flag=Yes," or "no", 268 "Set Cond Flag=No," based upon the answer to this inquiry. Return is then made to the main adaptive light level processing, 266 "Return" and 270 "Return," respectively, from the appropriate set condition flag direction 264 and 268.

If the histogram mean value is not less than the desired aim, then the processor proceeds from inquiry 258 to determine whether the mean value is greater than the aim and the filter curve is greater than filter curve 0, 272 "Hist Mn Val>Aim and Fltr Curve>0?" Assuming that both conditions are met, then the position of the filter curve index is decremented within the illumination lookup table and the intersection of the present subpoint with the upper filter curve is determined, 274 "Dec Fltr Curve Index; Calc Present Setpoint Intersect of Upper Curve." Inquiry is then made whether the histogram mean value is within the adjusted curves, 276 "Hist Mn Val within Adjusted Curves?" In response to this inquiry the condition flag is either set "yes", 278 "Set Cond Flag=Yes," or "no", 282 "Set Cond Flag=No," and return is made to the main adaptive light level program, 280 "Return" and 284 "Return," respectively.

If both conditions of inquiry 272 are not met, then the processor passes to inquiry 286 to determine whether the histogram mean value is greater than the desired aim and the filter curve index setting is zero, 286 "Hist Mn Val>Aim and Fltr Curve=0?" If "yes" then the illumination aperture wheel is physically adjusted a predefined number of motor steps, 288 "Physically Inc Aper," and the condition flag is set "yes", 290 "Set Cond Flag=Yes." From instruction 290, or alternatively, if the answer to inquiry 286 is "no," the processor reads the status of the condition flag, 292 "What is Cond Flag Status?" If the flag status is "no", then the present filter wheel is physically set to equal the filter curve index within the illumination lookup table, 294 "Physically Set Fltr=Fltr Curve Index." Subsequent instruction 294, or if the answer to inquiry 292 is "yes", processing returns to the main adaptive light level flow, 284 "Return."

Figure 10:
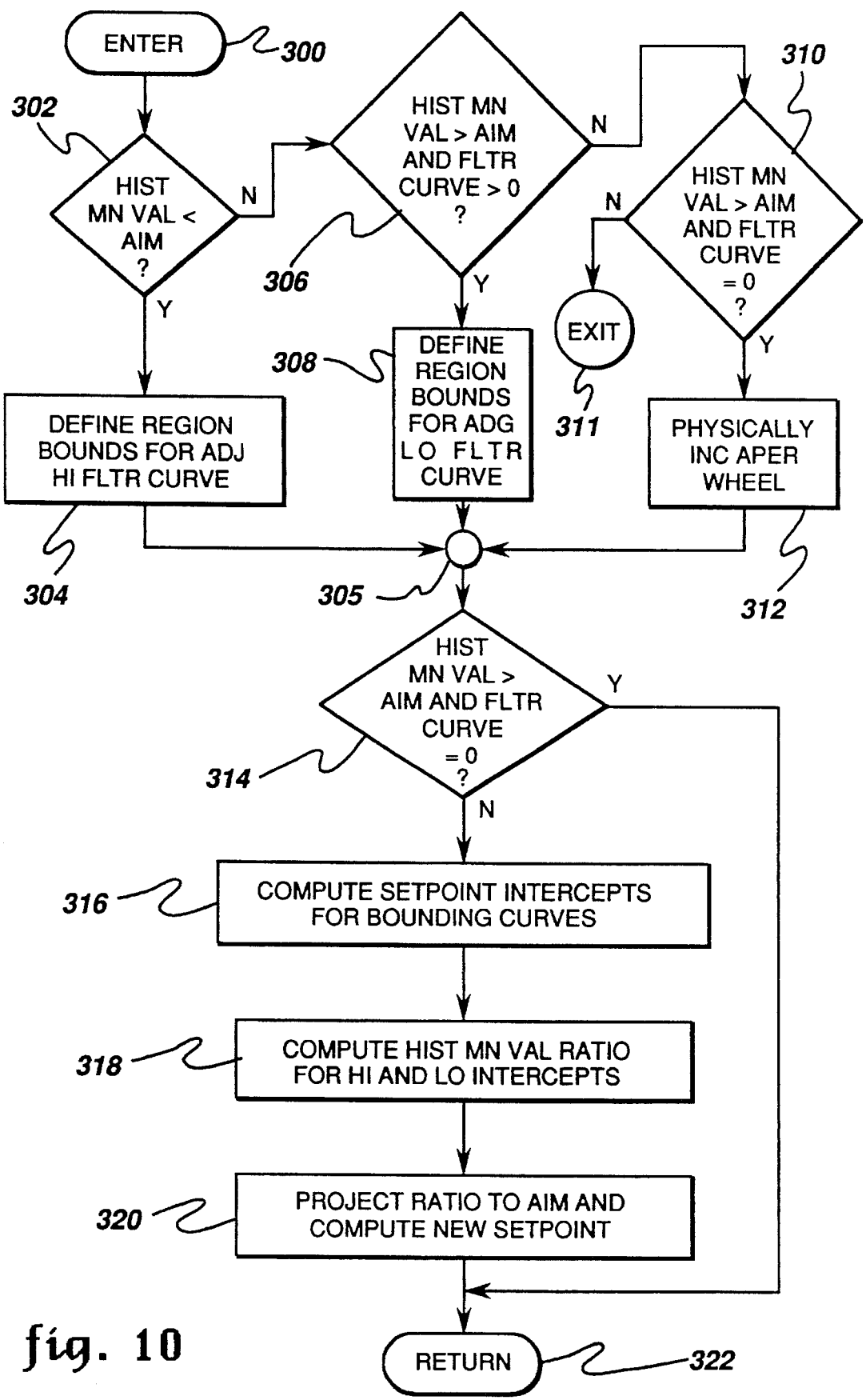
FIG. 10 is a flowchart of one embodiment of a recalculate setpoint subroutine for the adaptive light level process control of FIG. 8.

One embodiment of a calculate new setpoint subroutine is set forth in FIG. 10. After entering this subroutine, 300 "Enter," inquiry is made whether the histogram mean value is less than the desired aim value, 302 "Hist Mn Val<Aim?" If "yes" then the region bounds for the adjacent high filter curve are defined from the illumination lookup table, 304 "Define Region Bounds for Adj Hi Fltr Curve." From instruction 304, the processor passes to junction 305.

If the histogram mean value is not less than the desired aim, then the processor inquires whether the histogram mean value is greater than the desired aim and whether the present filter curve is other than filter curve 0, 306 "Hist Mn Val>Aim and Fltr Curve>0?" If "yes", then the region bounds for the adjacent lower filter curve are defined, 308 "Define Region Bounds for Adj Lo Fltr Curve," and processing proceeds to junction 305. If the histogram mean value is greater than the desired aim, but the filter curve value is not greater than the zero filter curve, then inquiry is made whether the filter curve equals the zero filter curve, 310 "Hist Mn Val>Aim and Fltr Curve=0?" If "no", then processing is terminated, 311 "Exit." Alternatively, if both conditions are met, then the processor is directed to physically increment the aperture wheel setting a predefined amount, 312 "Physically Inc Aper Wheel." After which, processing proceeds to junction 305. From junction 305 inquiry is made whether the histogram mean value is greater than the desired aim and the filter curve is equal to the zero filter curve, "Hist Mn Val>Aim and Fltr Curve=Zero?" If "no", then the setpoint intercepts for the bounding curves are computed, 316 "Compute Setpoint Intercepts for Bounding Curves," along with the histogram mean value ratio for both the high curve and low curve intercepts 318 "Compute Hist Mn Val Ratio for Hi and Lo Intercepts." From this information, a new setpoint is computed by projecting a ratio to the desired aim value, 320 "Project Ratio to Aim and Compute New Setpoint." After the setpoint has been computed, or if the answer to inquiry 314 is "yes", return is made to the main adaptive light level processing (FIG. 8), 322 "Return."

Figure 11:
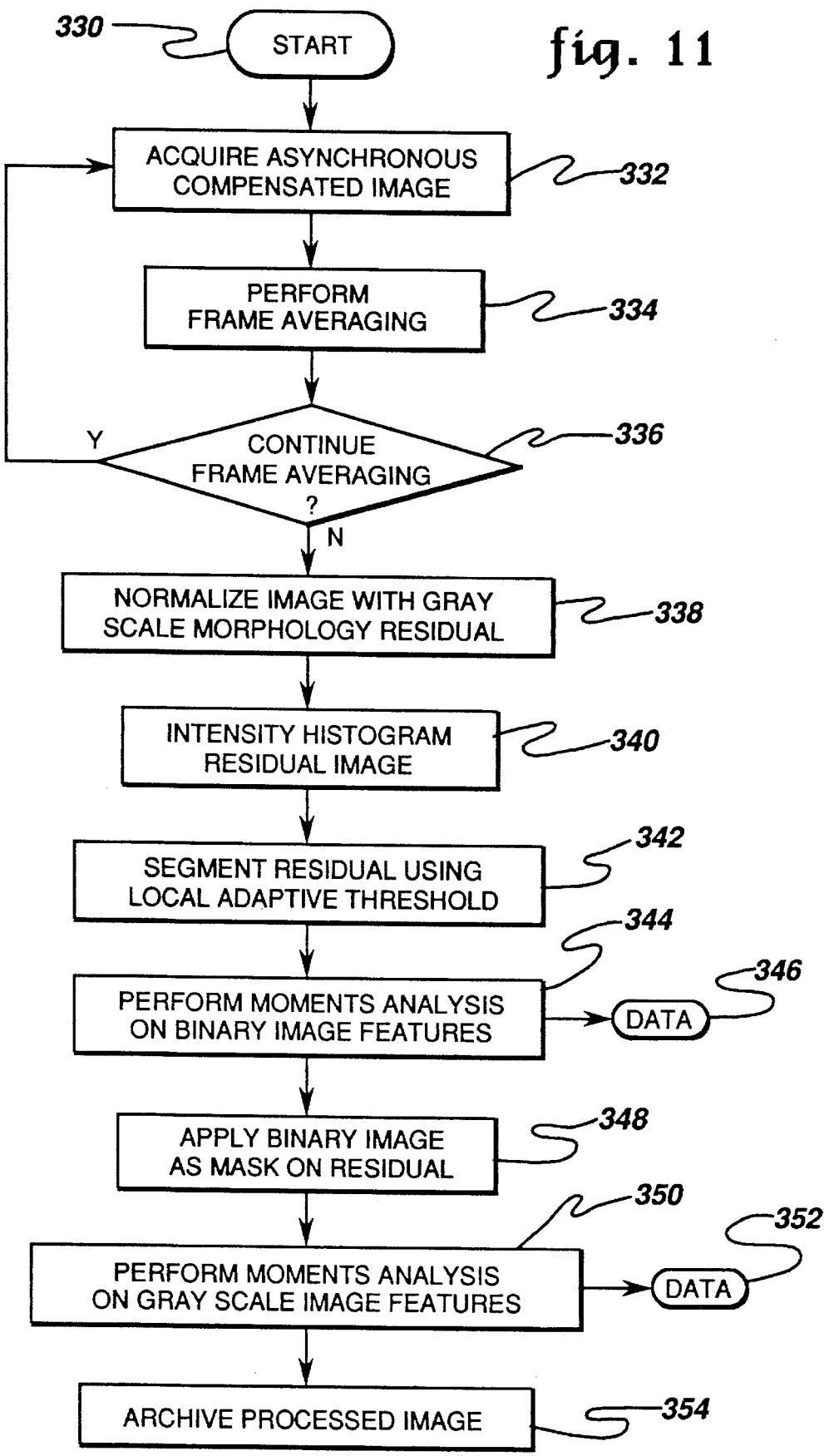
FIG. 11 is a flowchart of one embodiment of a coating density analysis algorithm, implemented in the image processor of FIG. 1, for identifying continuous-type coating anomalies pursuant to the present invention.
Figure 12A:
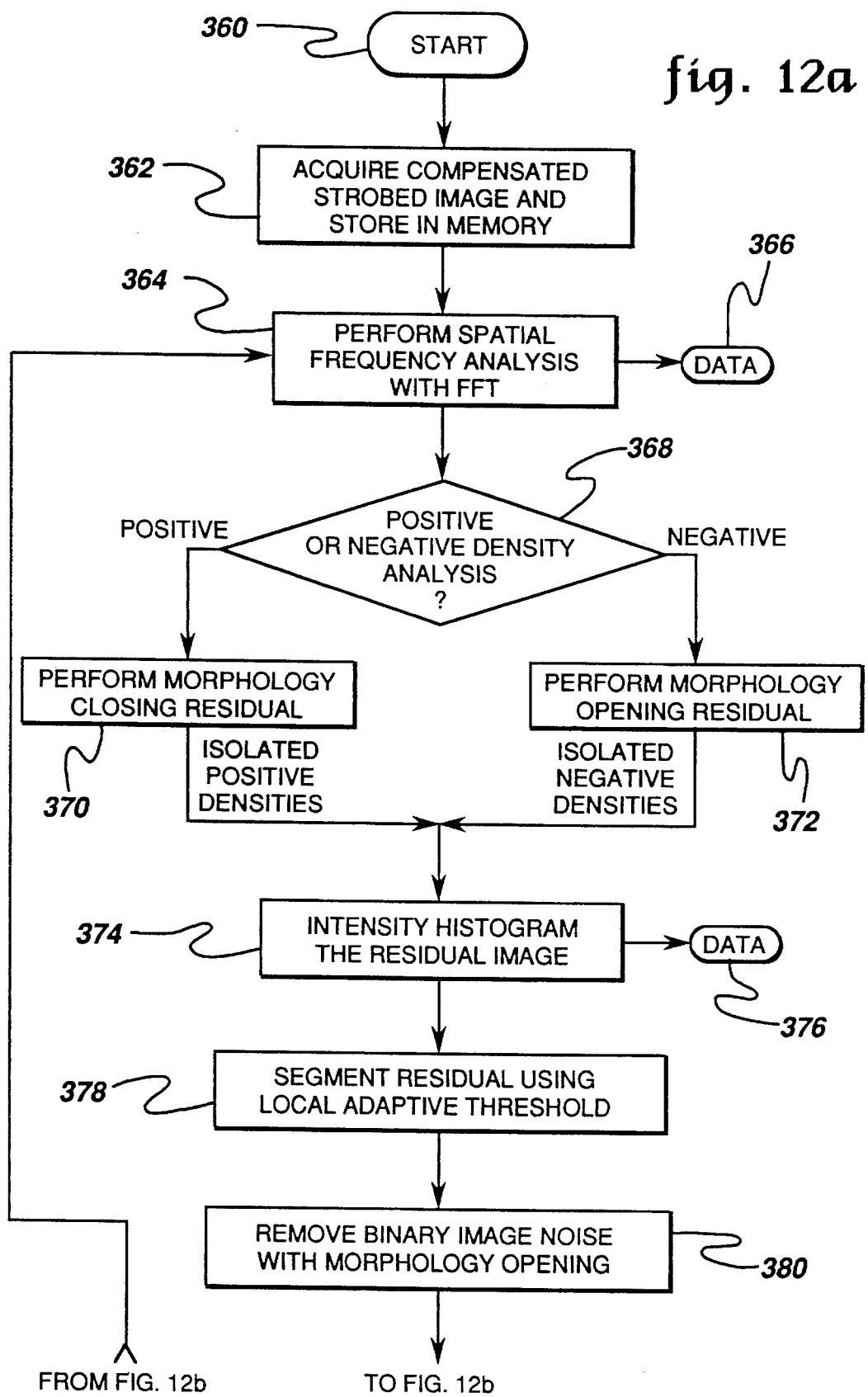
FIGS. 12(a) & 12(b) are a flowchart of one embodiment of a coating density analysis algorithm, implemented in the image processor of FIG. 1 for identifying point-type coating anomalies pursuant to the present invention.
Figure 12B:
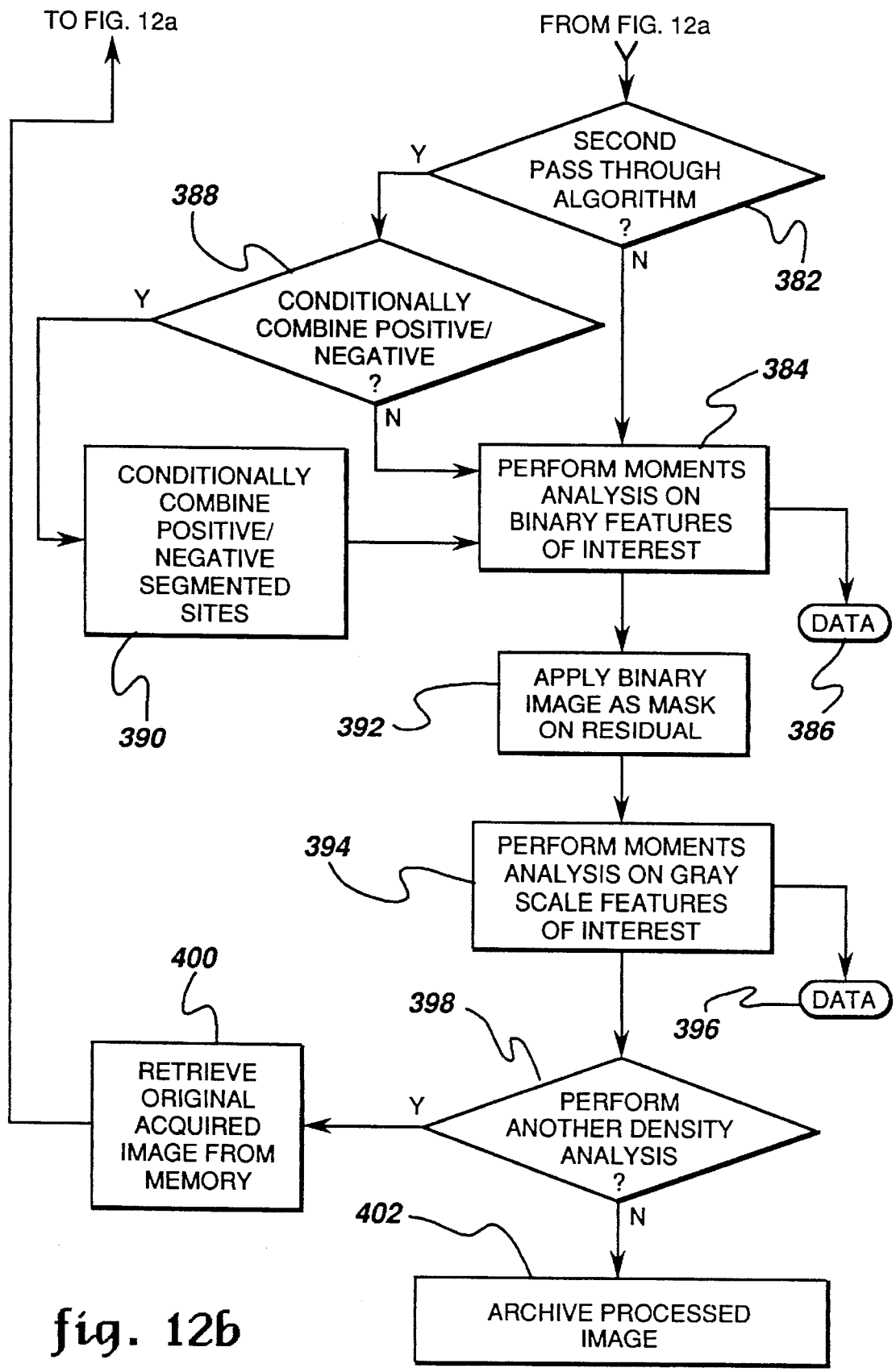

FIGS. 11, 12(*a*) & 12(*b*) depict processing overviews for automated processing of continuous-type and point-type coating density anomalies in a moving web material. Furthermore, the processing sequence for point-type imperfections is applicable to stationary web material. One skilled in the art can readily implement the noted image processing functions, where necessary, using information available in the open literature.

Depending upon the coating anomaly under study, certain geometric moments, intensity based statistics, and spatial frequency data derived from the algorithm set forth are of value in determining the extent and type of coating density artifacts. Those skilled in the art can use the automatic analysis algorithms of FIGS. 11, 12(*a*) & 12(*b*), or apply any one of a number of fundamental analysis tools accessible within an image processor's standard software library to perform image interpretation tasks. The information produced by the system provides quantitative data, as well as qualitative visual feedback in the form of displayed processed images, to an operator controlling machine process parameters, e.g., during coating experiments.

Referring specifically to FIG. 11, after processing is initiated, 330 "Start", an asynchronous compensated image is acquired using the solid state camera, 332 "Acquire Asynchronous Compensated Image." For continuous-type imperfections, temporal image frame averaging during asynchronous acquisition is employed to reduce random imaging noise artifacts, 334 "Perform Frame Averaging." Each digitized image is stored in the computer's frame buffer with preprocessing (gain and offset adjustment) controlling the expanded dynamic range of interest to be acquired. If frame averaging is to continue, 336 "Continue Frame Averaging?," the processor loops back via the "yes" path to instruction 332 to acquire another image. The image intensity can be directly related to product density in transmission imaging space because the digitized video signal may be passed through a logarithmic transform prior to being stored in the frame buffer.

Initially, the image is compensated by classical means using a stored reference image, where the reference has intrinsic image information regarding the system's optical imaging aberrations, CCD sensor response variability, and illumination intensity spatial variation. The resulting compensated image, with the imaging system errors removed, is properly conditioned for subsequent image coating density analysis.

The image is normalized using morphological opening or closing residual functions to selectively filter out relatively low spatial frequency density variations which are not the principle focus of study, 338 "Normalize Image With Gray Scale Morphology Residual." The gray scale morphology residual operation results in the desired isolation of the positive or negative density features of interest to be analyzed.

Intensity statistics derived from computing a bit-plane histogram of the residual image, 340 "Intensity Histogram Residual Image," are relevant for assessing the extent of an imperfections' density. The histogram moments may also be used for establishing a global minimum intensity level which is above the characteristic noise. From this, adaptive local segmentation methodologies may be applied for proper partitioning of binary features, 342 "Segment Residual Using Local Adaptive Threshold." A preferred method of segmenting the foreground features is defining the threshold intensity value at each individual pixel as the greater of either the global minimum noise intensity level or a value defined as a percentage of intensity strength at each pixel in a morphologically gray scale dilated version of the residual image. Geometric moments analysis can next be performed, 344 "Perform Moments Analysis on Binary Image Features" with the resultant data, 346 "Data," made available in memory for analysis. Information regarding average width is significant for characterizing continuous coating imperfections interpreted in the binary domain.

Utilizing the binary frame as a mask applied to the gray scale image, 348 "Apply Binary Image as a Mask on Residual," pertinent gray scale features in the image can be analyzed for their characteristic moments, 350 "Perform Moments Analysis on Gray Scale Image Features." Intensity based moment statistics of pixels in the gray scale frame corresponding to sites segmented in the binary frame are of value in determining the extent of the continuous imperfection. Additionally, the pixel intensity profile of the average of many pixel rows in the image is another means of determining the extent of a continuous coating imperfection. The resultant moments and averaged profile data, 352 "Data," are saved in memory for subsequent analysis.

As an option, resultant image information can be stored before proceeding with the acquisition of a next image, 354 "Archive Processed Image." Based on the histogram residual statistics, binary moments, and gray scale moments derived during the automatic processing of FIG. 11, interpretation of generated data permits coating process parameters to be adjusted in a logical manner to provide increased improvement in coating density uniformity expectations of a resultant product.

FIGS. 12(*a*) & 12(*b*) depict one embodiment of automated point-type coating density imperfection image analysis. In this algorithm, processing begins, 360 "Start", with the acquisition of a compensated strobed image which is stored into memory, 362 "Acquire Compensated Strobed Image and Store in Memory." For point-type imperfections, a strobed source or shuttered camera, is used to effectively 'freeze' the motion of the product being imaged from the camera's perspective. The expanded dynamic range of each acquired image is a result of preprocessing (gain and offset adjustment) that can be applied to the video signal. The image intensity can be directly related to product density in transmission imaging space because the digitized video signal may be passed through a logarithmic transform prior to being stored in the frame buffer.

The compensated gray scale image is typically analyzed within a region of interest in terms of its spatial frequency for its harmonics and bandpower measurements, 364 "Perform Spatial Frequency Analysis with FFT." The resultant data, 366 "Data", is saved in memory for subsequent analysis. The interpretation of this frequency information provides an operator with one of several means for determining the type and extent of the density imperfection. Furthermore, the spatial frequency harmonics may be used to determine the predominant size category of morphological structuring elements employed in subsequent filtering operations. By proper selection of the structuring elements baseline shape, size and intensity component profile, varying degrees of a given density imperfection class can be distinguished and isolated for subsequent image analysis operations.

Depending if positive or negative density analysis is selected, 368 "Positive or Negative Density Analysis?," the image is normalized using a closing residual, 370 "Perform Morphology Closing Residual," or opening residual, 372 "Perform Morphology Opening Residual," respectively, to selectively filter out relatively low spatial frequency density variations which are not the principle focus of study. The gray scale morphology residual operation results in the desired isolation of the positive or negative density features of interest to be analyzed.

Intensity statistics derived from computing a bit-plane histogram of the residual image, 374 "Intensity Histogram The Residual Image," are relevant for assessing the extent of the imperfection's density. The histogram moments may also be used for establishing a global minimum intensity level that is above the characteristic noise. (This data, 376 "Data", is saved in memory for subsequent analysis.) From this, adaptive local segmentation methodologies may be applied to the processed images for proper partitioning of binary features, 378 "Segment Residual Using Local Adaptive Threshold." A preferred method of segmenting the foreground features is defining the threshold intensity value at each individual pixel as the greater of either the global minimum noise intensity level or a value defined as a percentage of intensity strength at each pixel in a morphologically gray scale dilated version of the residual image. The resultant binary image may have remaining irrelevant noise artifacts removed by applying morphology opening operations or modified hit-or-miss transforms, 380 "Remove Binary Image Noise with Morphology Opening."

Referring to FIG. 13(b), if both positive and negative density have been segmented as a result of multiple algorithm passes, 382 "Second Pass Through Algorithm," an option is provided, 388 "Conditionally Combine Positive/Negative?," via the "Yes" path to conditionally combine adjacent positive and negative density sites, 390 "Conditionally Combine Positive/Negative Segmented Sites." This may be of value in isolating certain point-type imperfections with a given characteristic signature of light and dark density areas within a selected spatial adjacency factor. For imperfections identified as point-type, geometric moments analysis on the binary features, 384 "Perform Moments Analysis on Binary Features of Interest," is performed on either the positive or negative or conditionally combined density frame. The information extracted from the moment analysis such as the area, perimeter, aspect ratio, and eccentricity of individual sites in the binary frame is made available in memory for analysis, 386 "Data."

Utilizing the binary frame as a mask applied to the gray scale image, 392 "Apply Binary Image As Mask On Residual," pertinent gray scale features in the image can be analyzed for their characteristic moments, 394 "Perform Moments Analysis On Gray Scale Image Features of Interest." Intensity based moment statistics of pixels in the gray scale frame corresponding to sites segmented in the binary frame are of value in determining the extent of the point-type imperfection. Again, the resultant data, 396 "Data", is saved in memory for subsequent analysis. If another density analysis of the compensated input image is required, 398 "Perform Another Density Analysis?", the "yes" path instructs the processor to recall original image, 400 "Retrieve Original Acquired Image From Memory," and loop back to instruction 364 of FIG. 12(a).

As before, resultant image information can be stored before proceeding with the acquisition of a next image, 402 "Archive Processed Image." Based on the spatial frequency information, residual histogram statistics, binary moments, and gray scale moments derived from the automatic execution of the algorithm, the interpretation of the generated data permits coating machine process parameters to be adjusted in a logical manner to provide increased improvement in the coating density uniformity expectations of a resultant product.

Those skilled in the art will note from the above discussion that an image processor based technique (system and method) is set forth for imaging and analyzing any predefined type density anomaly in a coated web, including two-dimensional and one-dimensional-type imperfections. Specific density imperfections to be imaged may include continuous-type, as well as point-type, imperfections. The technique described can resolve variations in optical density of 0.0005. Significantly improved signal-to-noise characteristics over prior art implementations can be realized. Real time logarithmic image acquisition is utilized while still maintaining performance and system/process flexibility. On-line compensation for illumination intensity uniformity is featured. The imperfection recognition technique is readily implementable by one skilled in the art using existing hardware/software packages at a moderate cost expenditure.

Although several embodiments of the present invention have been illustrated in the accompanying drawings and described in the foregoing detailed description, it will be understood that the invention is not limited to the particular embodiments described herein, but is capable of numerous rearrangements, modifications and substitutions without departing from the scope of the invention. The following claims are intended to encompass all such modifications.

We claim:

1. An image processor based system having a two-dimensional imaging area, said system for recognizing a predefined continuous-type density imperfection in a coating on a moving coated web passing through said imaging area, said system comprising:

a non-coherent light source providing uniform illumination of said web while said web passes through said two-dimensional imaging area;

full-frame image acquisition and full-field integration means for accumulating coating density data representative of a plurality of different regions of said illuminated moving coated web, each region of said plurality of different regions being co-extensive, passing sequentially through said imaging area, and having a corresponding full-frame image, said full-field integration means for outputting integrated image data representative of a sum of said corresponding full-frame images; and an image processor coupled to said image acquisition and integration means, said image processor being programmed to recognize said at least one density imperfection of said predefined continuous-type in said coating using said integrated image data output by said integration means.

2. The system of claim 1, wherein said image processor includes:

a logarithmic amplifier for converting linear space analog image data received from said image acquisition and integration means to log space analog image data using digital processing, for use in recognizing said at least one density imperfection.

3. The image processor based system of claim 1, wherein the said coated web comprises a moving, continuous-type coated support web.

4. The image processor based system of claim 3, wherein said coated web comprises a photographic film web.

5. The image processor based system of claim 1, wherein said light source includes an adjustable illumination output and wherein said image processor is coupled to said light source and includes control means for controlling adjustment of said adjustable illumination output.

6. The image processor based system of claim 5, wherein said light source provides uniform transmissive illumination of said web.

7. The image processor based system of claim 6, wherein said uniform transmissive illumination provided by said light source has a nonuniformity of less than five percent.

8. The image processor based system of claim 5, wherein said image processor includes on-line means for programmably adjusting the intensity of said uniform illumination provided by said light source.

9. The image processor based system of claim 5, wherein said light source includes a wideband light illumination source and said system further comprises an integrating sphere having an input and an output, the output of said illumination source being optically coupled to the input of said integrating sphere, the output of said integrating sphere providing said uniform transmissive illumination of said web while said web passes through said imaging area.

10. The image processor based system of claim 9, wherein said wideband illumination source is coupled to said integrating sphere via a fiber-optic bundle.

11. The image processor based system of claim 9, wherein said uniform illumination of said web at the output of said integrating sphere is constant.

12. The image processor based system of claim 9, wherein said uniform illumination of said web at the output of said integrating sphere is strobed.

13. The image processor based system of claim 9, further comprising an illumination intensity adjustment mechanism disposed between said illumination source and said integrating sphere, said adjustment mechanism being responsive to said image processor means for programmable adjustment of the intensity of said uniform illumination provided by said light source.

14. The image processor based system of claim 13, wherein said image processor means for varying the illumination source intensity includes means for referencing a predefined lookup table of desired illumination intensities for various web densities, and wherein said illumination adjustment mechanism comprises a variable aperture control disposed at the output of said illumination source, said variable aperture control being responsive to said image processor.

15. The image processor based system of claim 1, wherein said full-frame image acquisition and integration means comprises a two-dimensional image acquisition and integration CCD camera.

16. The image processor based system of claim 15, wherein said two-dimensional image acquisition and integration CCD camera includes an integration function capable of both synchronous and asynchronous execution.

17. The image processing system of claim 2, wherein said logarithmic amplifier includes programmable gain and offset means for amplifying and offsetting said image data output by said image acquisition means.

18. The image processing system of claim 2, wherein said logarithmic amplifier further includes a lookup table for converting said image data from said linear space to said log space, said lookup table being predefined.

19. The image processing system of claim 2, wherein said logarithmic amplifier further includes a sync stripper for isolating a video signal in linear space from said image data output by said image acquisition means.

20. A method for recognizing a predefined-type density imperfection in a coating of a coated web as the coated web passes through an imaging area, said recognition method comprising the steps of:

(a) uniformly illuminating said coated web while the web passes through said imaging area with non-coherent illumination;

(b) acquiring full-frame coating density data on a plurality of different co-extensive regions of said illuminated web sequentially passing through said imaging area;

(c) full-field integrating said full-frame coating density data accumulated in said step (b) and producing based thereon integrated image data representative of a sum of said full-frame coating density data thereof; and (d) recognizing said predefined-type density imperfection in said coating from said integrated image data produced in said step (c).

21. The recognition method of claim 20, wherein said illuminating step (a) includes transmissively uniformly illuminating said web while said web passes through said imaging area.

22. The recognition method of claim 21, wherein said step (a) includes uniformly illuminating said web passing through said imaging area such that the illumination intensity on said web within said imaging area is constant, and wherein said density imperfection of predefined-type comprises a continuous-type density imperfection.

23. The recognition method of claim 22, wherein said density data acquiring step (b) includes two-dimensional imaging of said web while said web passes through said imaging area.

24. The recognition method of claim 20, further comprising the step of adaptively adjusting the illumination intensity within said imaging area based on the density of said web.

25. The recognition method of claim 24, wherein said step of adaptively adjusting said illumination intensity includes referring to an illumination lookup table of desired intensity levels for different density webs.

26. The recognition method of claim 20, wherein said predefined density imperfection comprises a point-type density imperfection and said step (a) includes providing a uniform strobed illumination of said web while passing through said imaging area.

27. The recognition method of claim 26, further comprising the step of normalizing the strobed illumination of said web within said imaging area.

28. The recognition method of claim 20, further comprising the step of converting said integrated image data produced in said step (c) from linear space to log space prior to said recognizing step (d).

29. The recognition method of claim 20, wherein said recognizing step (d) includes the steps of:

isolating predefined density-types of interest in said integrated image data produced in step (c);

performing fast fourier transform image analysis and size, shape and gray scale statistical analysis on individual sites within said imaging area for each isolated density-type of interest; and identifying said predefined density-type imperfections from said analysis performed on said density-types of interest.

30. The recognition method of claim 29, further comprising the step of evaluating the severity of any recognized, predefined density-type imperfection.

31. The recognition method of claim 29, wherein said analysis step includes performing moments analysis on the isolated density-types of interest.

32. An image processor based system having a two-dimensional imaging area, said system for recognizing a predefined continuous-type density imperfection in a coating on a moving coated web passing through said system comprising:

full-frame image acquisition and full-field integration means for accumulating coating density data representative of a plurality of different regions of said moving coated web, each region of said plurality of different regions being co-extensive, passing sequentially through said imaging area and having a corresponding full-frame image, said full-field integration means for outputting integrated image data representative of a sum of said corresponding full-frame images; and an image processor coupled to said image acquisition and integration means, said image processor being programmed to recognize said at least one density imperfection of said predefined continuous-type in said coating using said integrated image data output by said integration means.

33. A method for recognizing a predefined-type density imperfection in a coating of a coated web as the coated web passes through an imaging area, said recognition method comprising the steps of:

(a) uniformly illuminating said coated web while the web passes through said imaging area with non-coherent illumination;

(b) acquiring coating density data on a plurality of co-extensive regions of said illuminated web sequentially passing through said imaging area;

(c) integrating said coating density data accumulated in said step (b) and producing based thereon integrated image data representative thereof;

(d) isolating predefined density-types of interest in said integrated image data produced in said step (c);

(e) performing fast fourier transform image analysis and size, shape and gray scale statistical analysis on individual sites within said imaging area for each isolated density-type of interest; and (f) identifying said predefined density-type imperfections from said analysis performed on said density-types of interest.

34. The recognition method of claim 33, further comprising the step of evaluating the severity of any recognized, predefined density-type imperfection.

35. The recognition method of claim 33, wherein said analysis step includes performing moments analysis on the isolated density-types of interest.

* * * * *